(12) United States Patent
Aljohani

(10) Patent No.: US 9,417,161 B2
(45) Date of Patent: Aug. 16, 2016

(54) DRAINABLE SIGHT GLASS AND ASSOCIATED METHODS

(71) Applicant: Saudi Arabian Oil Company, Dhahran (SA)

(72) Inventor: Samer Mohammed Aljohani, Yanbu (SA)

(73) Assignee: Saudi Arabian Oil Company, Dhahran (SA)

( * ) Notice: Subject to any disclaimer, the term of this patent is extended or adjusted under 35 U.S.C. 154(b) by 193 days.

(21) Appl. No.: 14/347,377

(22) PCT Filed: Sep. 24, 2012

(86) PCT No.: PCT/US2012/056846
§ 371 (c)(1),
(2) Date: Mar. 26, 2014

(87) PCT Pub. No.: WO2013/048941
PCT Pub. Date: Apr. 4, 2013

(65) Prior Publication Data
US 2014/0238156 A1     Aug. 28, 2014

Related U.S. Application Data

(60) Provisional application No. 61/539,330, filed on Sep. 26, 2011.

(51) Int. Cl.
*G01N 1/00* (2006.01)
*G01N 1/10* (2006.01)
*G01F 23/02* (2006.01)

(52) U.S. Cl.
CPC . *G01N 1/10* (2013.01); *G01F 23/02* (2013.01)

(58) Field of Classification Search
None
See application file for complete search history.

(56) References Cited

U.S. PATENT DOCUMENTS 2,503,033 A * 4/1950 Engelmann ........ B29D 11/0074
138/148
4,981,040 A * 1/1991 Lin ......................... G01F 23/02
285/911

(Continued)

OTHER PUBLICATIONS

PCT International Search Report and the Written Opinion of the International Searching Authority dated Feb. 11, 2013; International Application No. PCT/US2012/056846; International File Date: Sep. 24, 2012.

*Primary Examiner* — Hezron E Williams
*Assistant Examiner* — Mark A Shabman
(74) *Attorney, Agent, or Firm* — Bracewell LLP; Constance Gall Rhebergen

(57) ABSTRACT

Embodiments of the invention are directed to methods of use and a (trainable sight glass assembly for use with a sump pump having a pump housing and being adapted to view the condition of oil disposed, within the pump housing. In some embodiments, the drainable sight glass assembly can comprise a sight glass housing having an upper disk layer with a first diameter and a first threaded receptacle formed therein disposed on a top side of the sight glass housing, a lower disk portion with a second diameter and a second threaded receptacle formed therein and disposed on a bottom side of the sight glass housing, and a substantially transparent wall portion connecting upper disk layer to the lower disk portion so that the sight glass has a hollow, substantially frustoconically shaped interior when oil is not in the sight glass housing.

16 Claims, 13 Drawing Sheets

(56) References Cited

U.S. PATENT DOCUMENTS

| | | | | |
|---|---|---|---|---|
| 5,036,883 A | * | 8/1991 | McHugh | A62C 35/68 |
| | | | | 137/557 |
| 5,243,929 A | * | 9/1993 | Brown | G01F 23/02 |
| | | | | 116/276 |
| 6,390,163 B1 | * | 5/2002 | Duddey | C08L 9/06 |
| | | | | 152/209.1 |
| 2003/0000315 A1 | * | 1/2003 | Leys | B29C 66/73921 |
| | | | | 73/861.57 |
| 2004/0083891 A1 | | 5/2004 | Welker | |
| 2008/0179344 A1 | | 7/2008 | Michaels et al. | |
| 2010/0313655 A1 | | 12/2010 | Welker et al. | |

\* cited by examiner

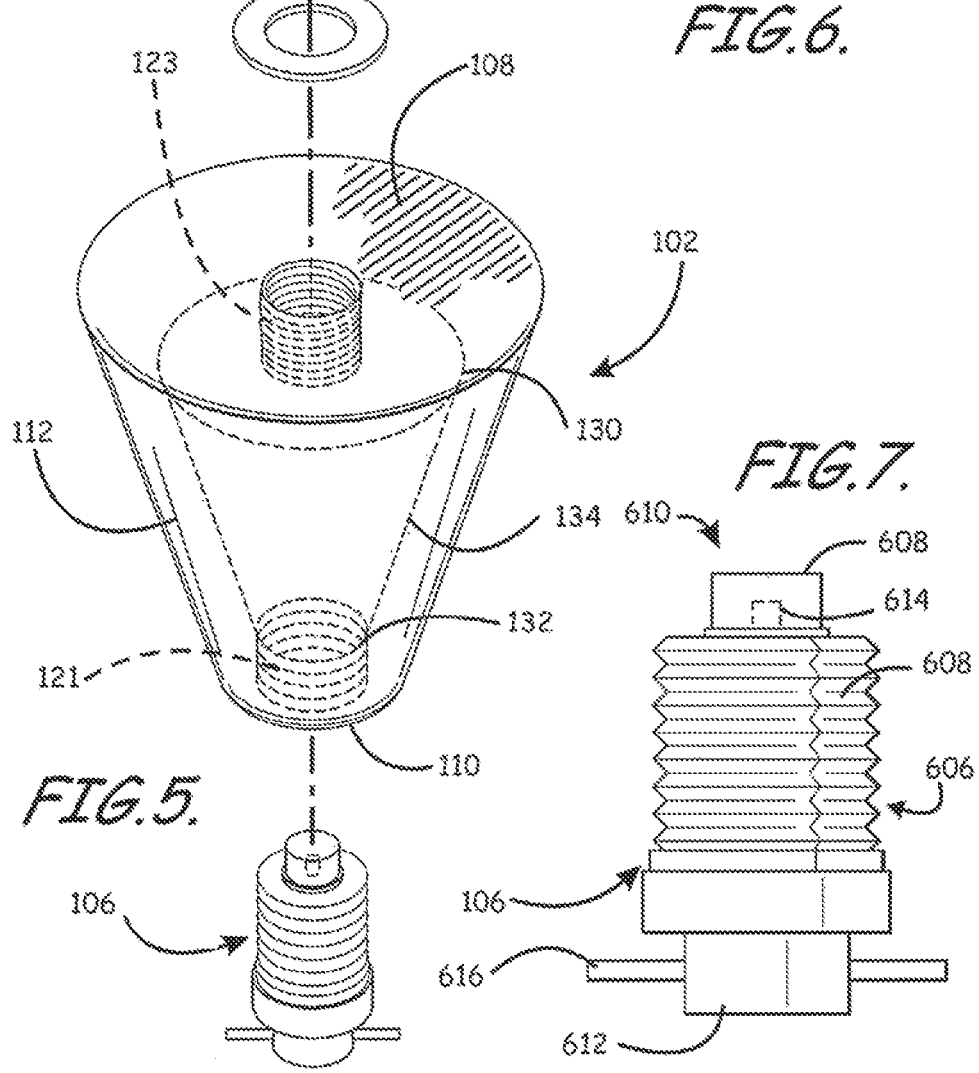
FIG.5.
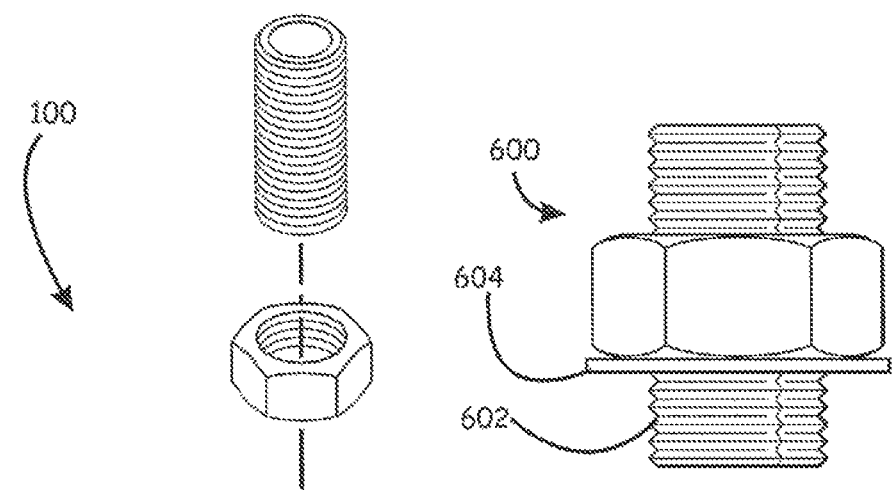
FIG.6.
FIG.7.

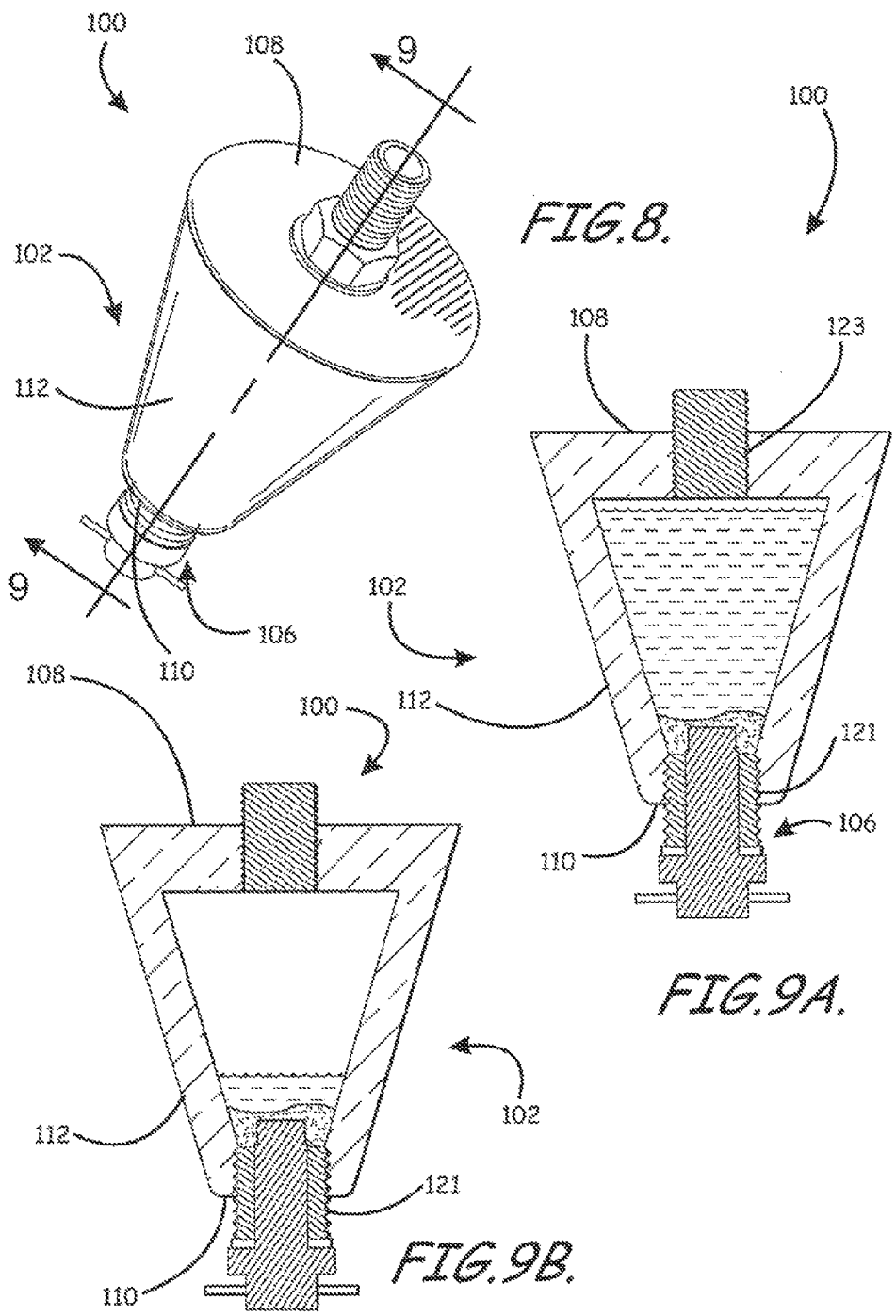

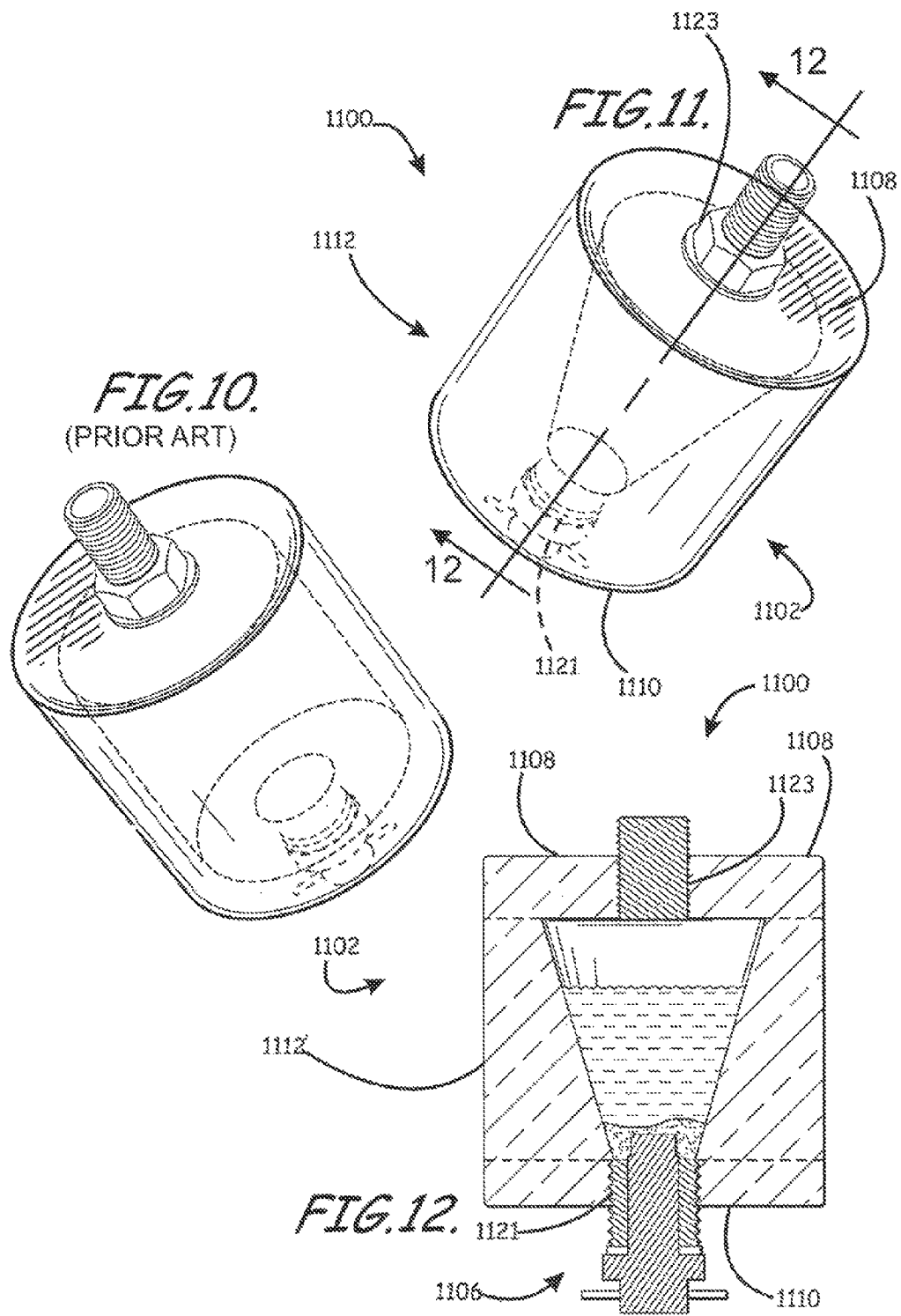

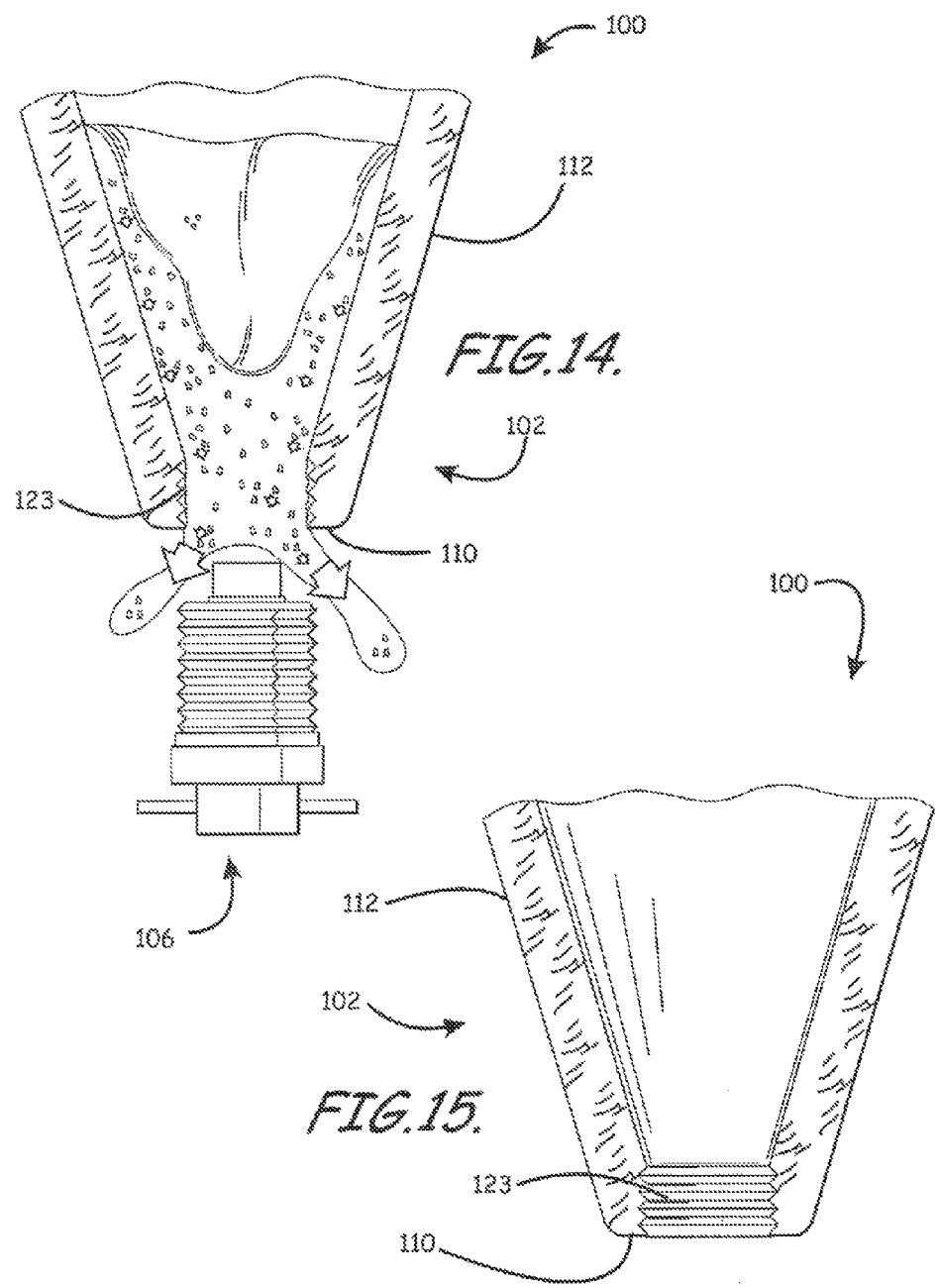

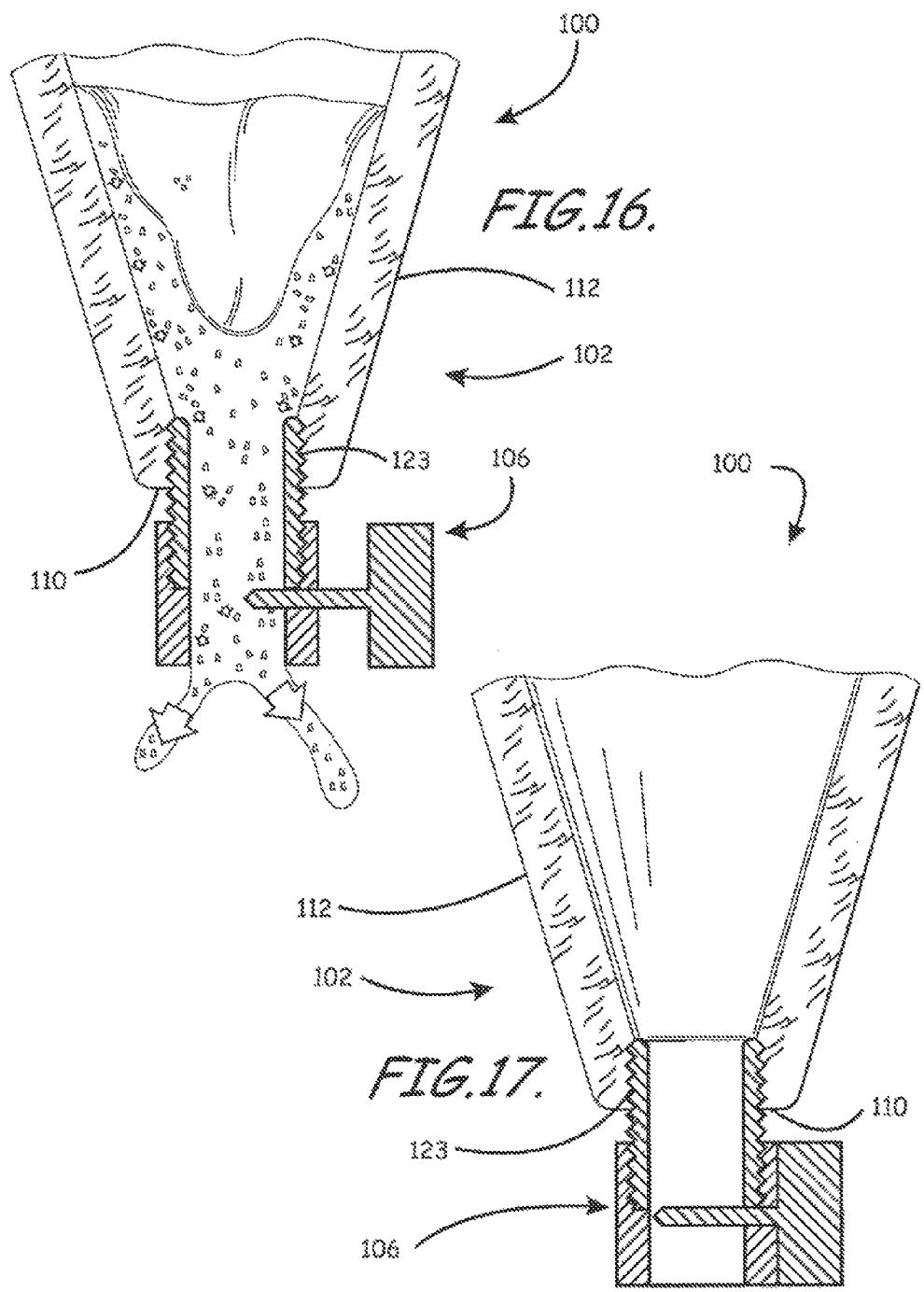

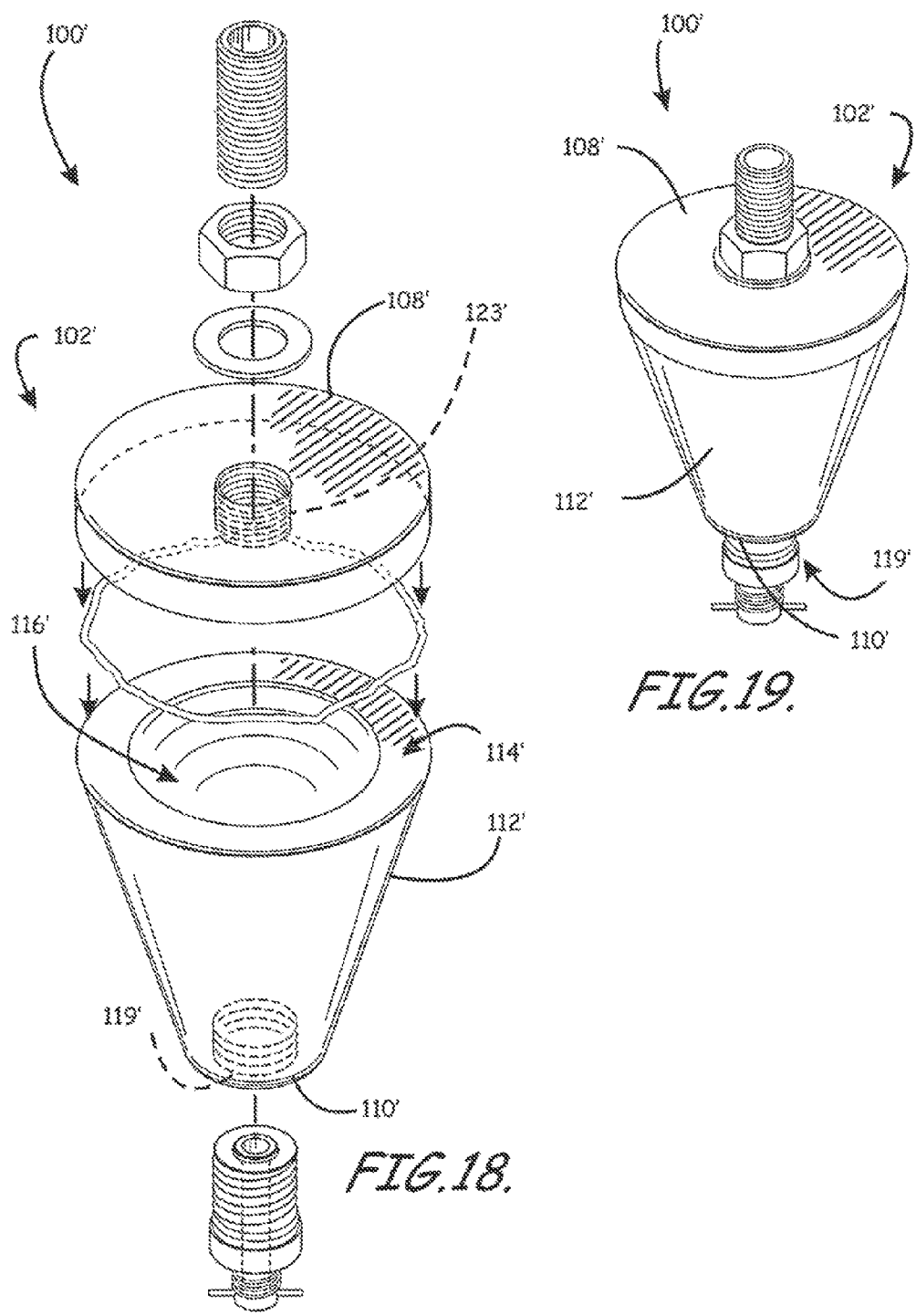

DRAINABLE SIGHT GLASS AND ASSOCIATED METHODS

RELATED APPLICATIONS

This application claims priority to and the benefit of: U.S. Provisional Patent Application Ser. No. 61/539,330, by Aljohani, titled "Drainable Sight Glass and Associate Methods" filed Sep. 26, 2011, and PCT Application Serial No. PCT/US12/56846, filed Sep. 24, 2012, both of which are incorporated herein by reference in their entirety.

FIELD OF INVENTION

The present invention relates generally to methods and apparatuses for monitoring the condition of oil in a housing, such as a pump motor housing, and more particularly to monitoring oil in a housing a frustoconically shaped sight glass.

BACKGROUND OF THE INVENTION

A drainable sight glass assembly and method for installation of such a sight glass on industrial machinery, e.g., oil sumps, oil reservoirs, and diesel fuel tanks, in the art is used to check the condition of oil in a pump or motor housing. In some prior art embodiments, the sight glass can also be used to separate oil and water. Such sight glasses include a top and bottom valve connected to a tubular shaped, transparent sight glass body. In use, oil is drained from the machinery housing into the sight glass through the valve. If water is in the sight glass, then a drain valve located at the bottom of the sight glass can be used to drain the water from the sight glass and thereby drain any water from the machinery housing. In addition, the sight glass can be used as a vessel to transport oil for testing by a laboratory to determine contaminants in the oil that can indicated oil wear.

Unfortunately, contaminants in the motor housing, e.g., dirt, can create a turbulent flow into and a sludge in the sight glass body making it difficult to view the oil for inspection and for water to separate from the oil for draining from the bottom valve. In addition, the creation of a sludge in the sight glass body can, over time, weaken the sight glass body, making the sight glass vulnerable to cracking and shattering. Moreover, if the piping to the sight glass gets clogged, there can be a false indication of oil condition, e.g., the oil in the sight glass can appear clean and pristine contrary to the condition of the oil in the sump. Many industrial applications, therefore, require a maintenance worker to frequently clean and replace the sight glass to prevent any accidental shattering of the sight glass.

The majority of sight glasses in the prior art are either the cylindrical type, discussed above, or used for measuring a level of fluid in a vessel without a means of draining fluid from the sight glass. For example, U.S. Pat. No. 5,406,844 (May et al.) describes drainable sight glass assembly and method for installation of such a sight glass for use in preventing contaminants from entering an injection-molding machine which is similar to the problematic prior art. This sight glass includes a top and bottom valve connects to a tubular shaped, transparent sight glass body, and therefore presents the same problems to the operator as those noted. U.S. Patent Publication 2010/053,786 (Schachinger) describes a drainable sight glass assembly for use in determining the fluid level in a high-pressure container. The sight glass is engaged in an opening in the vessel so that the sight glass forms a plane with the container wall, or alternatively is wedged into the container wall. There are no valves in Schachinger to allow for water to drain from the sight glass, and the pump housing, and accordingly, Schachinger cannot solve the problems noted above. U.S. Pat. No. 4,446,731 (Martin) describes a fluid container, e.g., in a pressurized air filter or lubricator, that has a transparent, angularly shaped, and longitudinally tapered sight glass disposed thereon to allow a user to determine the fluid level in the container. Martin also does not have valves for draining water from the sight glass and housing, and accordingly cannot solve the problems in the art noted above.

What is needed, therefore, is a sight glass that will allow any fluid contaminants in the sight glass to settle towards the bottom to thereby allow an operator to adequately view the material in the sight glass, allow for the separation of oil and water in the sight glass to aid in draining the water therefrom, and allow for the contaminants to be removed when the water is drained from the sight glass.

SUMMARY OF THE INVENTION

Embodiments of the invention are directed to a drainable sight glass assembly for use with a sump pump having a pump housing and being adapted to view the condition of oil disposed within the pump housing. In some embodiments, the drainable sight glass assembly can comprise a sight glass housing having an upper disk layer with a first diameter and a first threaded receptacle formed therein disposed on a top side of the sight glass housing, a lower disk portion with a second diameter and a second threaded receptacle formed therein and disposed on a bottom side of the sight glass housing, and a substantially transparent wall portion connecting upper disk layer to the lower disk portion so that the sight glass has a hollow, substantially frustoconically shaped interior when oil is not in the sight glass housing. In some embodiments, the sight glass can also comprise an upper valve connected to the drainable sight glass assembly at the first threaded receptacle, the upper valve having a upper stem to connect to the pump housing to actuate a plug valve disposed therein to allow the oil to flow from the pump motor into the frustoconically shaped interior and a lower valve connected to the drainable sight glass assembly at the second threaded receptacle, the lower valve having a valve housing with an inner threaded portion to engage a second stem and an outer threaded portion to engage the second threaded receptacle, a top portion of the stem being disposed in the valve housing and another bottom portion of the stem being positioned on the exterior of the sight glass and connected to a handle, the top portion of the stem having at least one opening formed therein so that when the top portion of the stem is disposed substantially inside the housing, the at least one opening is not exposed to the frustoconically shaped interior of the sight glass housing, and when the top portion of the stem is positioned so that the top portion of the stem is disposed outside of the valve housing in the interior of the frustoconically shaped sight glass, the at least one opening is exposed to the frustoconically shaped interior, the top portion of the stem being positioned substantially inside the valve housing or outside of the valve housing by turning the lower portion of the stem using the handle.

In other embodiments, a drainable sight glass assembly can have an upper disk layer and lower disk portion formed from the same material as the wall portion so that the upper disk layer, lower disk portion and wall portions are formed as an integral unit, and the upper disk layer and lower disk portion can be connected to the wall portion using adhesive, heat or solvents, and the adhesive is select from a group consisting of cyanoacrylate cement, or epoxy resin, the heat treatment is selected from a group consisting of welding or annealing, and the solvent is selected from a group consisting of dichloromethane or trichloromethane.

In other embodiments, the upper disk layer and lower disk portion can be selected from a group consisting of: stainless steel, aluminum, copper, polytetrafluoroethylene (e.g., Teflon®), and brass, and the upper disk layer and lower disk portion can be connected to the wall portion using one of heat or adhesive, the adhesive being select from a group consisting of cyanoacrylate cement or epoxy resin, and the heat treatment being selected from a group consisting of welding or annealing, so that the upper disk layer, lower disk portion and wall portion form a sealed vessel when connected to the lower valve and upper valve. In other embodiments, the wall portion can be formed from a group of materials selected from fiberglass, polycarbonate, glass, and acrylic. In some embodiments, the lower valve portion can be a spring valve and formed from a metal selected from the group of brass, copper, aluminum and steel, and the lower valve can have disposed thereon a magnetic coating that can be adapted to attract metallic particles in the oil when oil is disposed in the sight glass housing.

In other embodiments, the upper valve can have an upper valve housing disposed on the first upper valve stem, the upper valve housing being selected from a T valve or L valve having three ports, a first port being connected to the first threaded receptacle, the second port being connected to a measurement assembly for measuring the volume of oil in the housing, and a third port connected to the upper valve stem. Such a T valve or L valve can be used to switch a flow of the oil from the drainable sight glass assembly to the measurement assembly when the sight glass housing is full of oil. In some of these embodiments, the upper valve portion can be formed from a metal selected from the group of brass, copper, aluminum, and steel and the upper stem can be further connected to a pitot tube extending into the pump housing. Such a pitot tube can be used to sample oil from a portion of the housing vertically transposed from pump drain plug, and the drainable sight glass assembly can be vented to relieve pressure from the drainable sight glass assembly and allow the upper valve housing to switch the flow of oil from the drainable sight glass assembly to the measurement assembly.

Other embodiments of a drainable sight glass assembly for use with a sump pump having a pump housing and being adapted to view the condition of oil disposed within the pump housing are also described herein. Such an assembly can include a sight glass housing having an upper disk layer with a diameter and a first threaded receptacle formed therein disposed on a top side of the sight glass housing, a lower disk portion having the diameter of the first disk layer and a second threaded receptacle formed therein and disposed on a bottom side of the sight glass housing, and a substantially transparent wall portion connecting upper disk layer to the lower disk portion and having a first thickness near the top side of the sight glass housing and a second thickness near the bottom side of the sight glass housing so that the sight glass has a hollow, substantially frustoconically shaped interior when oil is not in the sight glass housing; an upper valve connected to the drainable sight glass assembly at the first threaded receptacle, the upper valve having a upper stem to connect to the pump housing to actuate a plug valve disposed therein to allow the oil to flow from the pump motor into the frustoconically shaped interior; and a lower valve connected to the drainable sight glass assembly at the second threaded receptacle, the lower valve having a valve housing with an inner threaded portion to engage a second stem and an outer threaded portion to engage the second threaded receptacle, a top portion of the stem being disposed in the valve housing and another bottom portion of the stem being positioned on the exterior of the sight glass and connected to a handle, the top portion of the stem having at least one opening formed therein so that when the top portion of the stem is disposed substantially inside the housing, the at least one opening is not exposed to the frustoconically shaped interior of the sight glass housing, and when the top portion of the stem is positioned so that the top portion of the stem is disposed outside of the valve housing in the interior of the frustoconically shaped sight glass, the at least one opening is exposed to the frustoconically shaped interior, the top portion of the stem being positioned substantially inside the valve housing or outside of the valve housing by turning the lower portion of the stem using the handle. In other embodiments, a drainable sight glass assembly can have an upper disk layer and lower disk portion formed from the same material as the wall portion so that the upper disk layer, lower disk portion and wall portions are formed as an integral unit, and the upper disk layer and lower disk portion can be connected to the wall portion using adhesive, heat or solvents, and the adhesive is select from a group consisting of cyanoacrylate cement, or epoxy resin, the heat treatment is selected from a group consisting of welding or annealing, and the solvent is selected from a group consisting of dichloromethane or trichloromethane.

In embodiments of such an assembly, the upper disk layer and lower disk portion can be selected from a group consisting of: stainless steel, aluminum, copper, polytetrafluoroethylene (e.g., Teflon®), and brass, and the upper disk layer and lower disk portion can be connected to the wall portion using one of heat or adhesive, the adhesive being select from a group consisting of cyanoacrylate cement or epoxy resin, and the heat treatment being selected from a group consisting of welding or annealing, so that the upper disk layer, lower disk portion and wall portion form a sealed vessel when connected to the lower valve and upper valve. In other embodiments, the wall portion can be formed from a group of materials selected from polycarbonate, glass, and acrylic. In some embodiments, the lower valve portion can be a spring valve and formed from a metal selected from the group of brass, copper, aluminum and steel, and the lower valve can have disposed thereon a magnetic coating that can be adapted to attract metallic particles in the oil when oil is disposed in the sight glass housing.

In other embodiments of such an assembly, the upper valve can have an upper valve housing disposed on the first upper valve stem, the upper valve housing being selected from a T valve or L valve having three ports, a first port being connected to the first threaded receptacle, the second port being connected to a measurement assembly for measuring the volume of oil in the housing, and a third port connected to the upper valve stem. Such a T valve or L valve can be used to switch a flow of the oil from the drainable sight glass assembly to the measurement assembly when the sight glass housing is full of oil. In some of these embodiments, the upper valve portion can be formed from a metal selected from the group of brass, copper, aluminum, and steel and the upper stem can be further connected to a pitot tube extending into the pump housing. Such a pitot tube can be used to sample oil from a portion of the housing vertically transposed from pump drain plug, and the drainable sight glass assembly can be vented to relieve pressure from the drainable sight glass assembly and allow the upper valve housing to switch the flow of oil from the drainable sight glass assembly to the measurement assembly.

Embodiments of a method for using a sight glass with a pump housing to monitor the condition of oil in the pump housing and to drain water from such a housing are described herein, also. Such a method can comprise connecting an upper valve positioned in a sight glass housing to the drain port of the housing, the sight glass housing having a top side with a large diameter top opening sealed with a upper disk layer having a threaded receptacle formed therein for receiving the upper valve, a bottom side with a small diameter bottom opening sealed with a lower disk portion sized substantially similarly to the upper disk layer and having a second threaded receptacle formed therein for receiving a lower valve, a lower valve connected to the drainable sight glass assembly at the second threaded receptacle, the lower valve having a valve housing with threads to engage the second threaded receptacle and a stem, a top portion of the stem being disposed in the valve housing and another bottom portion of the stem being positioned on the exterior of the sight glass and connected to a handle, the top portion of the stem having at least on opening formed therein so that when the top portion of the stem is disposed substantially inside the housing, the at least one opening is not exposed to the frustoconically shaped interior of the sight glass housing, and when the top portion of the stem is positioned so that the top portion of the stem is disposed outside of the valve housing in the frustoconical interior of the sight glass, the at least one opening is exposed to the frustoconically shaped interior, and a substantially transparent wall portion connecting the top side to the bottom side and the large diameter top opening to the small diameter bottom opening so that the sight glass has a hollow, substantially frustoconically shaped interior when fluid is not in the drainable sight glass assembly; draining oil into the sight glass using the upper valve in conjunction with the housing drain port; viewing the contents of the sight glass to determine the condition of the oil in the sight glass and whether or not water is present; and turning the lower portion of the stem handle of the lower valve when it is determined that water is in the sight glass to expose the top portion of the stem being disposed substantially inside the valve housing to the interior of the frustoconically shaped sight glass interior to drain water from the sight glass.

Embodiments of the method can also comprise the steps of removing the sight glass from the housing drain plug, responsive the water being drained; and testing the oil in the sight glass to determine a mechanical cause and location of for any contaminants being present in the oil. Embodiments of the method can also comprise the steps of removing the sight glass from the housing drain plug; and reintroducing the oil in the sight glass to the housing when the water is drained from the sight glass and when it is determined that the condition of the oil in the sight glass is acceptable for continued use. Embodiments of the method can comprise the steps of removing the sight glass from the housing drain plug; draining the water and oil from the sight glass, separably so as to save the oil so that the oil can be tested for contaminants; cleaning the sight glass so that any residue formed thereon by the oil and any contaminants is removed; and reattaching the sight glass to the housing drain plug. Other embodiments of the method can also during the cleaning of the sight glass, remove contaminants attached to a magnet on the lower valve stem for testing in addition to the oil.

BRIEF DESCRIPTION OF THE DRAWINGS

So that the manner in which the features and advantages of the invention, as well as others, which will become apparent, can be understood in more detail, a more particular description of the invention briefly summarized above can be had by reference to the embodiments thereof, which are illustrated in the appended drawings, which form a part of this specification. It is to be noted, however, that the drawings illustrate only various embodiments of the invention and are therefore not to be considered limiting of the invention's scope as it can include other effective embodiments as well.

FIG. 3A is a top perspective view of a sight glass having a frustoconically shaped interior installed on a pump housing and having a closed lower valve and an open upper valve according to an embodiment of the invention;

FIG. 3B is a top perspective view of a sight glass having a frustoconically shaped interior installed on a pump housing and having a closed lower valve and an closed upper valve according to an embodiment of the invention;

FIG. 3C is a top perspective view of a sight glass having a frustoconically shaped interior installed on a pump housing and having an open lower valve and a closed upper valve according to an embodiment of the invention;

FIG. 5 is an exploded view of a sight glass having a frustoconically shaped interior showing the various components thereof, including a upper valve, lower valve, and sight glass body, according to an embodiment of the invention;

FIG. 6 is a side view of an upper valve used to connect a sight glass having a frustoconically shaped interior to a pump housing according to an embodiment of the invention;

FIG. 7 is a side view of a lower valve used to drain fluid from a sight glass having a frustoconically shaped interior and a pump housing according to an embodiment of the invention;

FIG. 8 is a perspective view of a sight glass having a frustoconically shaped interior of an embodiment of the invention;

FIG. 9A is a side view of a sight glass having a frustoconically shaped interior of FIG. 8 showing a fluid, water and sediment disposed in the sight glass according to an embodiment of the invention;

FIG. 9B is a side view of a sight glass having a frustoconically shaped interior showing a fluid being drained from the sight glass body according to an embodiment of the invention;

FIG. 10 is a top perspective view of a sight glass having a cylindrical-shaped interior and a cylindrical exterior according to the prior art;

FIG. 11 is a top perspective view of a sight glass having a frustoconically-shaped interior and a cylindrical exterior according to an embodiment of the invention;

FIG. 12 is a side view of a sight glass having a frustoconically-shaped interior of FIG. 11 and a cylindrical exterior according to an embodiment of the invention;

FIG. 14 is a side view of a sight glass having a frustoconically shaped interior showing a fluid being drained from the sight glass body according to an embodiment of the invention;

FIG. 15 is a side view of a sight glass body having a frustoconically shaped interior showing threads in the sight glass body for receiving a lower valve according to an embodiment of the invention;

FIG. 16 is a side view of a sight glass having a frustoconically shaped interior showing a fluid being drained from the sight glass body according to an embodiment of the invention;

FIG. 17 is a side view of a sight glass body having a frustoconically shaped interior showing threads in the sight glass body for receiving a lower valve according to an embodiment of the invention;

FIG. 18 is an exploded view of a sight glass having a frustoconically shaped interior showing the various components thereof, including a upper valve, lower valve, and sight glass body, according to an embodiment of the invention;

FIG. 19 is a perspective view of a sight glass assembly having an upper valve used to connect a sight glass having a frustoconically shaped interior to a housing and a lower valve for draining the sight glass according to an embodiment of the invention.

DETAILED DESCRIPTION

Figure 1:
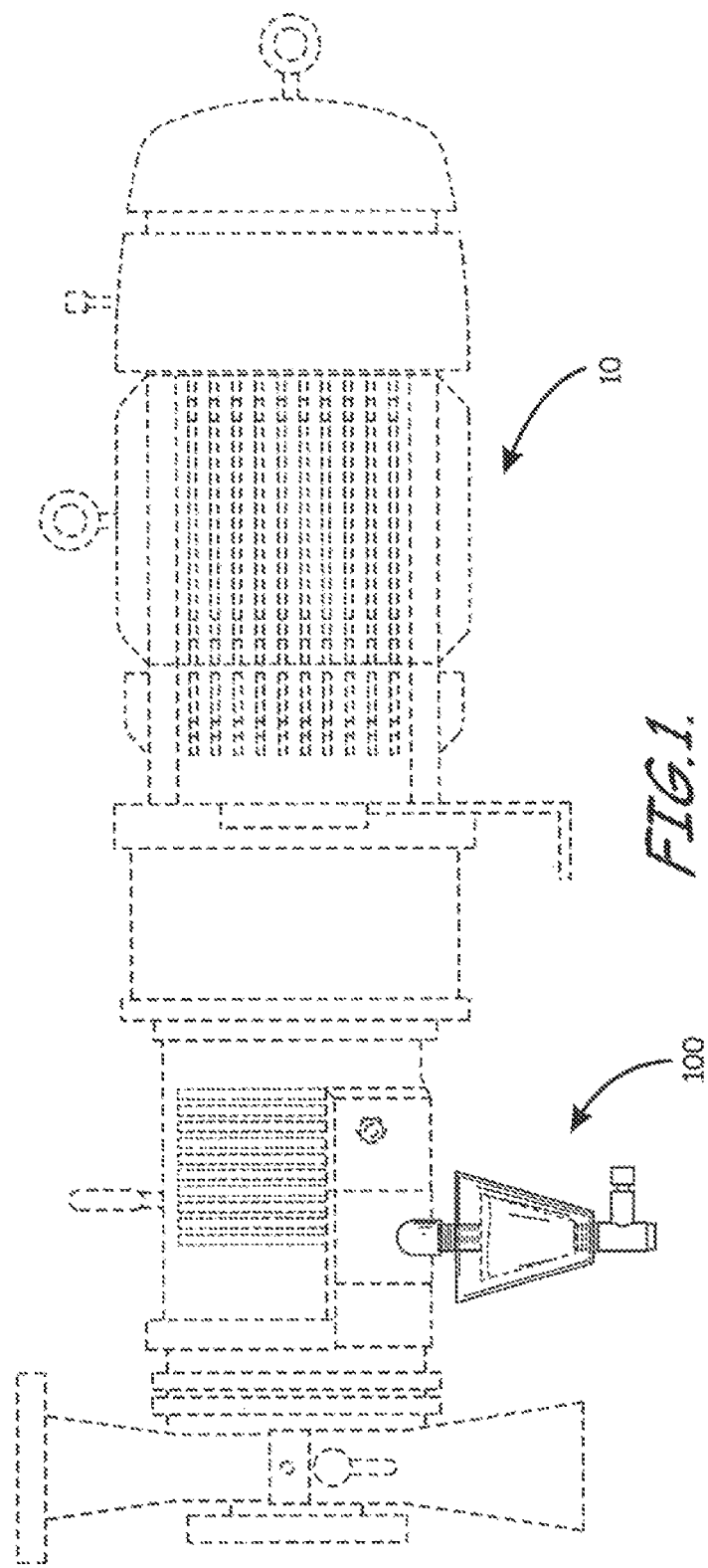
FIG. 1 is a side perspective view of a sight glass having a frustoconically shaped interior that tapers to a minimum diameter at a lower end equal to the outer diameter of a lower valve, and that does not have interior shoulders or other geometry capable of trapping contaminates or other debris in the sight glass, the sight glass installed on a pump housing according to an embodiment of the invention.

The present invention will now be described more fully hereinafter with reference to the accompanying drawings in which embodiments of the invention are shown. This invention can, however, be embodied in many different forms and should not be construed as limited to the illustrated embodiments set forth herein; rather, these embodiments are provided so that this disclosure will be thorough and complete, and will fully convey the scope of the invention to those skilled in the art.

Embodiments of the invention are directed to a frustoconically-shaped, drainable sight glass and associated methods such as to install on or use in association with fluid lubricating machinery to assist in determining the condition of fluid in the vessel. For example, the sight glass can be used to monitor the condition of oil in a lubrication system of an industrial pump. An embodiment of a sight glass, for example, can have a sight glass body that includes a sight glass body, for example, a ring layer, positioned in a medial portion of the sight glass body, a long diameter disk layer, fabricated from, for example, metal, and a short diameter disk layer, also fabricated from, for example, metal. Each disk layer can be positioned to abuttingly contact at least portions of respective opposing ends of the sight glass body. The sight glass body has an upper end portion substantially the same size as the long diameter disk layer, a lower end portion substantially the same size as the short diameter disk layer, and an interior chamber to allow fluid to be reside therein so that the shape of the sight glass body defines a substantially frustoconically-shaped and hollow housing when fluid is not positioned in the interior chamber. Each of the respective disk layers of the sight glass body, for example, also can be connected to the transparent ring using gaskets or through a process of being fused during manufacture as understood by those skilled in the art. In addition, an embodiment of a sight glass includes a first valve connected to the long diameter disk layer via, e.g., threads, to provide fluid access to the interior chamber and a second valve connected to the short diameter disk layer to inhibit or prevent fluid from departing the interior chamber when positioned therein. In other embodiments, the sight glass can be extruded with a frustoconically-shaped interior portion, and threads to attach the valves. In such an embodiment, for example, one or more of the disk layers would be unnecessary. In addition, the outer shape of the sight glass body, in some embodiments, can have a ring shape or other shape as long as the peripheries of the interior chamber have a substantially frustoconical, conical, or related shape to provide structural and functional aspects noted herein. In such embodiments, for example, the disk layers can have a similar size.

In operation, the first valve is opened when the sight glass is connected to the drain plug valve of the housing to allow fluid, for example, oil, to pass into the interior chamber of the housing of the sight glass body, and the second valve is normally in a closed valve position to thereby prevent fluid from flowing from the second valve to thereby allow the sight glass to fill with fluid and indicate condition of fluid in a vessel and yet allow sediment or particulate in the fluid to settle toward the lower end portion of the sight glass body to enhance fluid visibility in the sight glass. The normally closed second valve can be opened using a predetermined condition to allow fluid to drain from the housing when a predetermined condition is met, for example, when water is settling near the bottom of the sight glass. In this embodiment of the invention, for example, the combination of a transparent ring layer to view the contents of the sight glass body and the substantially frustoconical or conical shape of the ring layer to help substantially reduce or minimize turbulence in the housing and aid in draining, enhancing performance of this embodiment of the sight glass.

Turning to the Figures, a drainable sight glass assembly 100 for use with industrial machinery, e.g., oil sumps, oil reservoirs, and diesel fuel tanks is described therein, though one skilled in the art will recognize that the sight glass described herein can be used to monitor the condition of any fluid in a reservoir. As shown in FIGS. 1-5, 18 and 19 the drainable sight glass assembly 100 is used to view the condition of, for example, oil used in, for example, a pump housing 10, and can include a sight glass housing 102, upper valve 104 and lower valve 106. As one skilled in the art will appreciate, the drainable sight glass assembly 100 can be adapted for use without an upper valve 104, and such upper valve 104 can only be an attachment means for connecting the sight glass housing 102 to a drain port 12 on the housing 10. In other embodiments, the lower valve 106 and upper valve 104 can be dual ported or triple ported, or a combination of dual and triple ported, i.e., the upper valve 104 is triple ported and the lower valve 106 is dual ported, the upper valve 104 is dual ported and the lower valve 106 is triple ported, etc. As one skilled in the art will also appreciate, the upper valve 104 can be an attachment means that is capable of being mated with a pitot tube to, e.g., reach oil in the reservoir that is not contaminated with any sludge or contaminants that can be collecting in the bottom of same, with the bottom valve being connected to, for example, a drain valve and a jar to collect any deposits from the sight glass. Accordingly, though the embodiments described by the figures contemplate both the lower and upper valves being dual ported, not all such embodiments of the invention will be used with dual ported valves.

As further shown in FIGS. 2-5, in some embodiments of the invention, a sight glass housing 102 can be a portion of the drainable sight glass assembly 100 comprising a vessel that is capable of holding a fluid drained from the housing. As such, the sight glass housing 102 can include an upper disk layer 108, and a sight glass body 112, having a lower disk portion 110. The upper disk layer 108 can be a substantially cylindrically shaped body, having a diameter greater than its length, and adapted to receive an upper valve (discussed below) to attach the sight glass to the pump housing. Accordingly, the upper disk layer 108 can be disposed on a top side 114 of the sight glass housing 102 in abutting contact with the sight glass body 112, and can have a threaded receptacle 123 formed substantially in the center thereof for receiving the upper valve. The upper disk layer 108 substantially can cover and seal a large diameter opening 116 in the sight glass body 112 when the drainable sight glass assembly 100 is disposed in communication with the housing drain port and the upper valve 104 is not open to the sight glass housing 102.

In some embodiments, the large diameter opening 116 can be sized to have a diameter between 1.0 inches to 2.5 inches, and the upper disk layer 108 can be sized to have a diameter between 1.4 inches to 3.0 inches if, for example, the sight glass body 112 is designed to have an overall height between 3 to 4 inches and a an interior height of 2.5 inches, to hold a one to three ounce testing volume. As one skilled in the art will recognize, a lower disk portion 110 used in such a drainable sight glass assembly 100 can have a thickness or length between 0.25 to 0.7 inches. In some embodiments, the upper disk layer 108 has a threaded receptacle 123 formed therein for receiving either the complementary threads of the housing drain port or the upper valve 104. The upper disk layer 108 can be manufactured from acrylic, polytetrafluoroethylene (e.g., Teflon®), steel, aluminum, brass, copper, and other similar materials using, e.g., extrusion techniques, welding, molding, die casting and other known manufacturing techniques as appropriate for the material and application of use for the drainable sight glass assembly 100.

As further shown, in some embodiments, the sight glass housing 102 includes a lower disk portion 110. The lower disk portion 110 can be a substantially cylindrically shaped body, having a diameter greater than its length, and adapted to receive a lower valve (discussed below) to drain water from the pump housing. The lower disk portion 110 can have disposed substantially in the center thereof a threaded receptacle 121, which can be designed to receive the lower valve 106, and accordingly, the lower disk portion 110 is disposed on a bottom side 117 of and in abutting contact with the sight glass body 112. The lower disk portion 110 formed to, e.g., substantially cover, and seal a small diameter opening 119 in the sight glass housing when the sight glass housing 102 is disposed in communication with the lower valve 106, and the lower valve 106 is not open to the sight glass housing 102, e.g., is not in a position to drain the sight glass housing 102.

In some embodiments, the small diameter opening 119 of the sight glass body 110 can be sized to have a diameter between 0.4 inches to 0.75 inches, and the lower disk portion can be sized to have a diameter between 0.70 inches to 1.25 inches, if, e.g., the sight glass body 112 is designed to have an overall height between 3 to 4 inches and an interior height of 2.5 inches, to, for example, hold a one to three ounce testing volume. As one skilled in the art will recognize, a lower disk portion used in such an exemplary sight glass can have a thickness or length between 0.25 to 0.7 inches. In some embodiments, the lower disk portion 110 can also have the threaded receptacle 121 formed therein for receiving the complementary threads of the lower valve 106. The lower disk portion 110 can be manufactured for acrylic, polytetrafluoroethylene (e.g., Teflon®), steel, aluminum, brass, copper, and other similar materials using, e.g., extrusion techniques, welding, molding, die casting and other known manufacturing techniques as appropriate for the material and application of use for the drainable sight glass assembly 100.

Returning to the Figures, the sight glass body 112 is connected to the upper disk layer 108 comprises an upper side 130 that has the large diameter opening formed therein and a lower side 132 that has the small diameter opening formed therein, and a wall portion 134. As previously mentioned, the upper diameter opening can be sized between the small diameter opening 117 can be sized to be between 0.4 inches to 0.75 inches, and the large diameter opening can be sized to be between 1.0 inches to 2.5 inches, if, e.g., the sight glass body 112 is designed to have an overall height between 3 to 4 inches and a an interior height of 2.5 inches, to, e.g., hold a one to three ounce testing volume. The exterior of the upper side and lower side of the sight glass body 112 can have measurements to match the upper disk layer 108 and lower disk portion 110, e.g., a similar top and bottom diameter, giving the sight glass body wall a thickness of no less then, e.g., 0.2 inches. In some embodiments, the exterior of the upper side and lower side can be smaller than the corresponding upper disk layer 108 and lower disk portion 110, e.g., when the upper disk layer 108 and lower disk portion 110 include flanges that circumscribe and extend over a portion of the sight glass body 112 to allow the upper disk layer 108 and lower disk portion 110 to connect to the sight glass body 112 using, e.g., adhesive. As one skilled in the art will appreciate, the sight glass body 112 is preferably manufactured from a transparent material that is in each case suited for the application in which the sight glass body 112 is installed. For example, in high temperature applications, e.g., for temperatures exceeding 150 degrees Fahrenheit, the sight glass body 112 can be manufactured from, e.g., pyrex, while in other applications, the sight glass body 112 can be manufactured from, for example, acrylic, glass, or the like. Depending upon the material used, the sight glass body 112 can be manufactured using known extrusion, injection molding, compression molding and pressing and blowing techniques.

As one skilled in the art will recognize, the upper disk layer 108, or in some embodiments a separable lower disk portion 110, can be adhered to the sight glass body 112 using, for example, adhesive such as, for example, cyanoacrylate cement, more commonly known as superglue, Loctite® or epoxy resin, with heat (welding or annealing), or by using solvents such as dichloromethane or trichloromethane, depending upon the material used for the upper disk layer 108, lower disk portion 110, and sight glass body 112. As one skilled in the art will also appreciate, some of the above embodiments of the upper disk layer 108 and lower disk portion 110 are for applications where the fluid tested is not at an extreme temperature, or the type of fluid is not volatile. As such, embodiments of the invention can include sight glasses acceptable for extreme temperature or volatile fluid applications, and as such, the upper disk layer 108 and lower disk portion 110 can be machined and connected to the sight glass body 112 in such a manner to protect the sight glass body 112.

For example, the upper disk layer 108 and lower disk portion 110 can be fabricated from, e.g., steel or polytetrafluoroethylene (e.g., Teflon®), and connected to the sight glass body 112 using an industrial type of adhesive capable of withstanding high temperature. In other embodiments, the upper disk layer 108 and lower disk portion 110 may be machined with a larger diameter than the sight glass body 112 so that a portion of the upper disk layer 108 and lower disk portion 110 extends past an exterior edge of the sight glass body 112. In such an embodiment, the upper disk layer 108 and lower disk portion 110 may have a plurality of holes formed in the portion of the upper disk layer 108 and lower disk portion 110 extending past the sight glass body 112 to accommodate a plurality of screws that may connect the upper disk layer 108 and lower disk portion 110 around the periphery of the sight glass body 112, and secure same using, e.g., bolts, as is known in the art.

In other embodiments, one or more of the upper disk layer 108 and lower disk portion 110 can be formed from the same material as the wall portion 134 using, e.g., an extrusion technique, so that the upper disk layer 108, lower disk portion 110 and wall portion 134 are formed as an integral unit and, when connected to the upper valve 104 and lower valve 106, form a vessel capable of being sealed. In other embodiments, the upper disk layer 108 and lower disk portion 110 may have a colored coating disposed thereon so that water in the sight glass may be easily viewed. In any case, when the upper disk layer 108 and bottom disk layer are joined to the sight glass body 112 using, for example, the methods described above, the drainable sight glass assembly 102 has a hollow; substantially frustoconically shaped interior 90 when fluid is not in the drainable sight glass assembly 102.

Returning to FIGS. 2, 6 and 7, an upper valve 104 is connected to the sight glass body 112 at the threaded receptacle 123. As is shown, the upper valve 104 can include a threaded pipe fitting 600 adapted to attach the sight glass to the drain plug of the housing 10 and to operate a check or drain plug valve 12 in same, a bolt 602 and a washer 604. As one skilled in the art will appreciate, the upper valve 104 can also be a separate drain valve, which can or cannot be vented to allow for pressure dissipation, to further control flow of fluid into the sight glass body 112. The threaded pipe fitting 600 can be sized to fit in the threaded receptacle 123 in the upper disk layer 108, e.g., 0.2 inches to 0.5 inches in diameter, with a length greater than 0.75 inches, as can be required by the size of the drain port 12 in the housing. The threaded pipe fitting 600 can be manufactured from, for example, steel, brass, copper or the like, depending upon the fluid being tested. As is shown in FIG. 6, in some embodiments the threaded pipe fitting 600 has disposed thereon at least one bolt 602 and washer 604 for securing the pipe fitting the sight glass body 112. As one skilled in the art will recognize, such a bolt 602 and washer 604 assembly can be used to prevent over tightening of the pipe fitting 600 into the complementary threaded receptacle 123 in the upper disk layer 108 and shear or stress that can be applied to the upper disk layer 108 or sight glass body 112 from same. As one skilled in the art will also appreciate, the bolt 602 can be manufactured, for example, from steel, brass, copper or the like, and the washer 604 can be manufactured, for example, from vulcanized rubber, thermoplastic, or other such material. Both the bolt 602 and washer 604 are sized to engage the threaded pipe fitting 600.

In some embodiments, the upper valve 104 can include an L-port three-way ball or plug valve in addition to the threaded pipe fitting, as shown in FIGS. 3A-3C. Such a plug or ball valve can include an upper valve housing 300 with threads 302 to engage the first threaded receptacle and an upper valve stem 304, with a top portion 306 of the upper valve stem 304 being disposed in the upper valve housing 300 and another bottom portion 308 of the upper valve stem 304 being positioned on the exterior of the sight glass 100 and connected to a handle 310. The top portion 306 of the upper valve stem 304 has, for example, at least one opening 310 formed therein so that when the top portion 306 of the upper valve stem 304 is disposed substantially outside the housing 300, and the opening 310 is not exposed to the drain plug 12. When the top portion 306 of the upper stem 304 is positioned so that the top portion 306 of the stem is disposed inside of the valve housing 300, the at least one opening is exposed to the drain plug 12. The top portion 304 of the upper valve stem 304 is disposed substantially inside the upper valve housing 300 or outside of the upper valve housing 300 by, e.g., pushing or turning the lower portion of the upper valve stem using the handle 310. As one skilled in the art will appreciate, the upper valve 104 can be, for example, a plug or spring valve manufactured in the art and sized to be used in the application, e.g., the threads on the upper valve 104 attaching same to the upper disk layer 108 and sight glass body 112 is between 0.2 inches and 0.5 inches. The upper valve 104 can be manufactured from, for example, a metal selected from the group of brass, copper, aluminum and steel.

Figure 2:
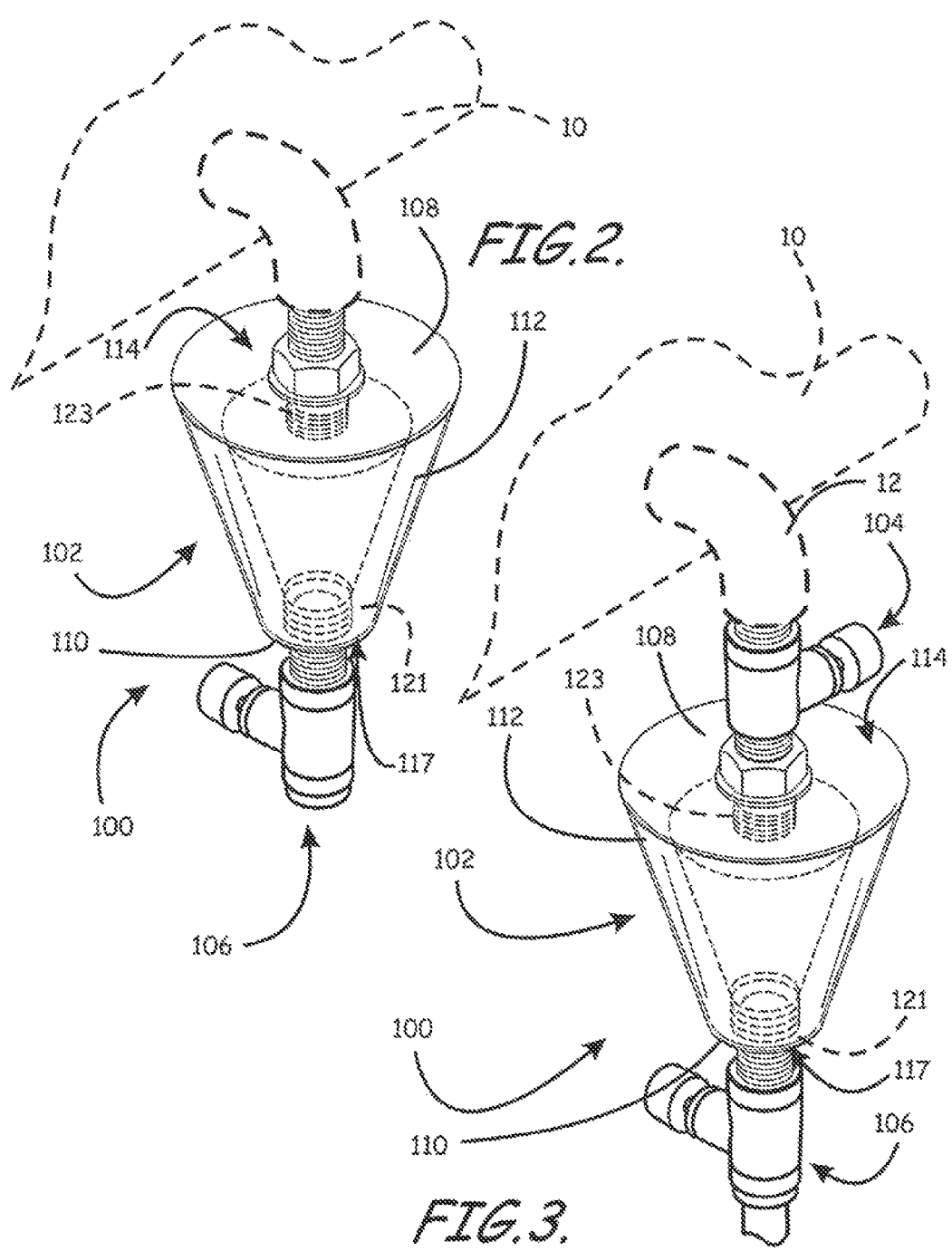
FIG. 2 is a top perspective view of a sight glass having a frustoconically shaped interior installed on a pump and having a lower valve according to an embodiment of the invention.
Figure 3:
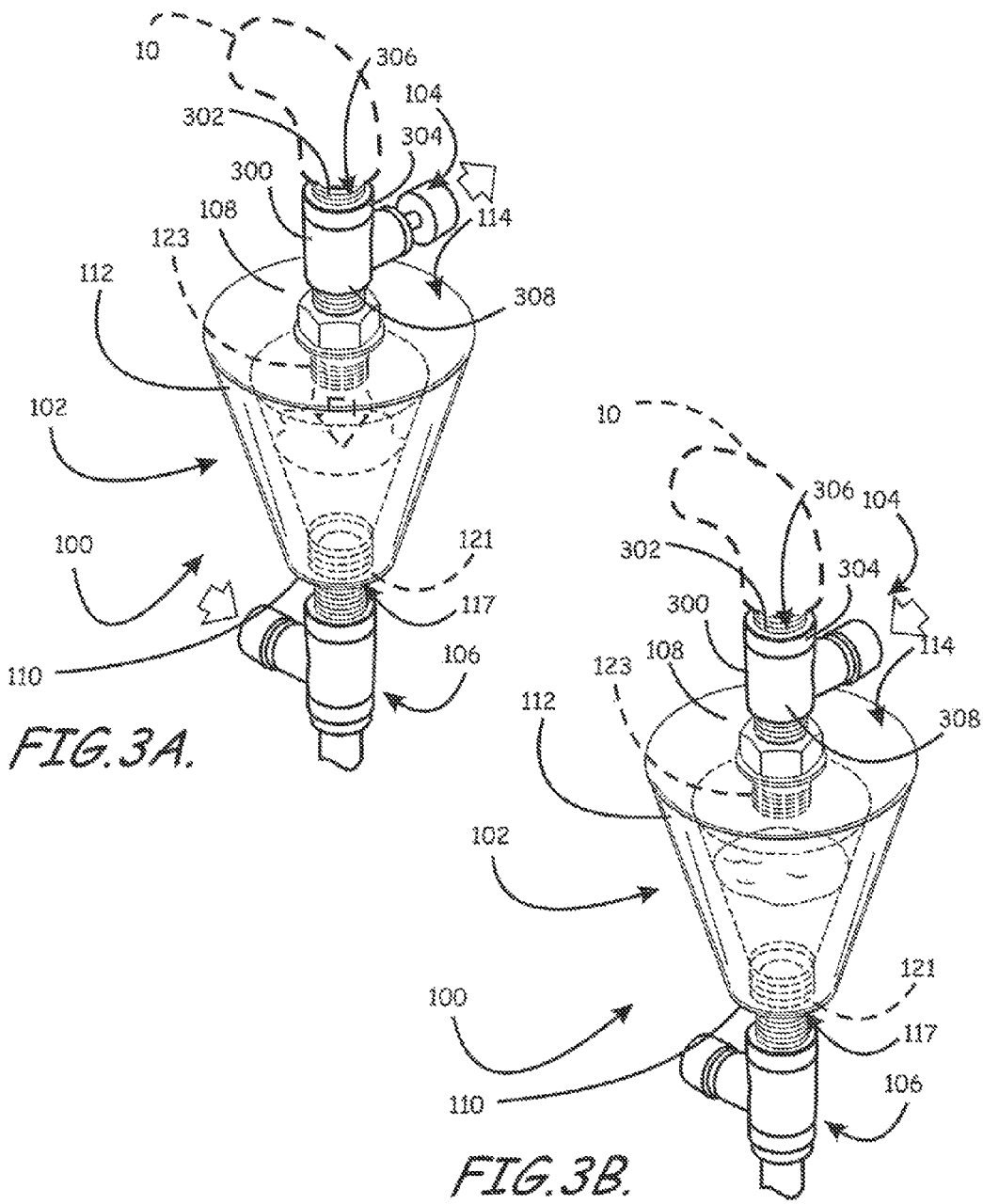
FIG. 3 is a top perspective view of a sight glass having a frustoconically shaped interior installed on a pump and having a lower valve and an upper valve according to an embodiment of the invention.
Figure 4:
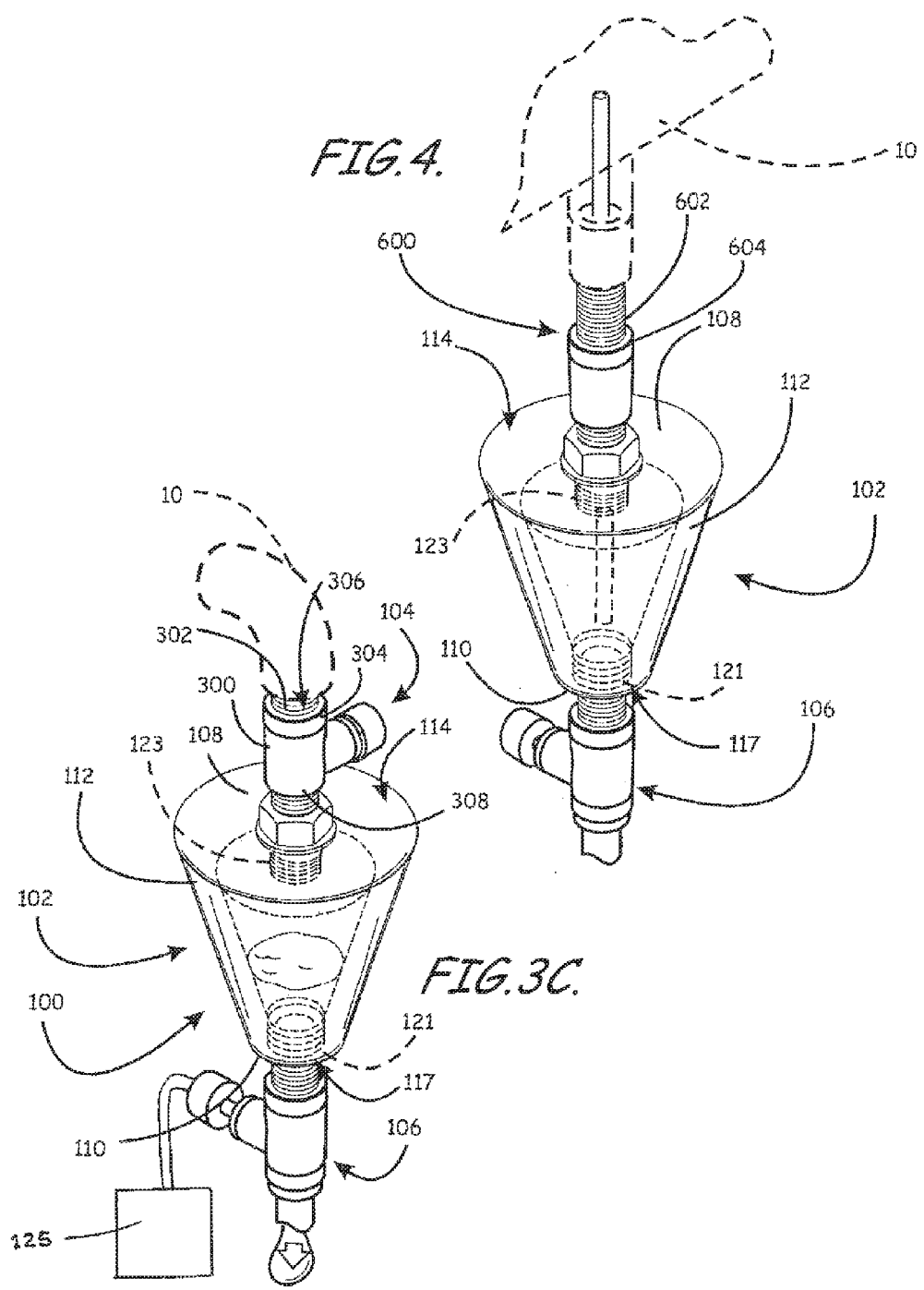
FIG. 4 is a top perspective view of a sight glass having a frustoconically shaped interior installed on a pump housing and having a pitot tube extending to an upper valve to collect oil or fluid from a position removed from a bottom of the pump housing, according to an embodiment of the invention.

As shown in FIGS. 2, 3 and 6, a lower valve 106 is connected to the drainable sight glass assembly at the second threaded receptacle 121. The lower valve 106 includes a valve housing 606 with threads 608 to engage the second threaded receptacle 121 in the lower disk portion 110 and sight glass body 112 and a stem 608, a top portion 610 of the stem being disposed in the valve housing 606 and another bottom portion 612 of the stem 608 being positioned on the exterior of the sight glass 126 and connected to a handle 616. The top portion 610 of the stem 608 has at least one opening 614 formed therein so that when the top portion 610 of the stem 608 is disposed substantially outside the housing 606, the at least one opening 614 is not exposed to the frustoconically shaped interior 90 of the sight glass housing 102, and when the top portion 610 of the stem 608 is positioned so that the top portion 610 of the stem 608 is disposed inside of the valve housing 606, the at least one opening is exposed to the frustoconically shaped interior 90. The top portion 610 of the stem 608 is disposed substantially inside the valve housing 606 or outside of the valve housing 606 by, e.g., pushing or turning the lower portion of the stem 608 using the handle 616. As one skilled in the art will appreciate, the lower valve 106 can be, for example, a plug or spring valve manufactured in the art and sized to be used in the application, e.g., the threads on the lower valve 106 attaching same to the lower disk portion 110 and sight glass body 112 is between 0.2 inches and 0.5 inches. The lower valve 106 can be manufactured from, for example, a metal selected from the group of brass, copper, aluminum and steel.

As one skilled in the art will appreciate, and as shown in FIGS. 3A-3C, in some embodiments, the upper valve 104 can include an L-port three-way ball or plug valve in addition to the threaded pipe fitting. In such embodiments, the sight glass can be connected to the drain plug 12 of the housing 10 with an L-port three-way ball or plug valve, where one position of the valve connects the drain plug 12 to the sight glass 100, and the other position drains the sight glass 100 to a container, such as, for example, measurement assembly 125. In other embodiments, the three-way valve may be the lower valve 110, so that when the upper valve is open to the drain plug 12, e.g., oil, will flow to the sight glass 100. To check the condition of both the fluid, and optionally, the fluid level, the lower valve can be repositioned to direct flow to a container, which drains the sight glass 100. The upper valve may be then repositioned to the drain plug allowing oil to flow back to the sight glass for a true reading of the oil level.

In alternative embodiments, a drainable sight glass assembly for use with, e.g., a pump motor can comprise a sight glass housing having a top side with a large diameter top opening sealed with a upper disk layer having a threaded receptacle formed therein, a bottom side with a small diameter bottom opening sealed with a lower disk portion sized substantially similarly to the upper disk layer and having a second threaded receptacle formed therein, and a substantially transparent wall portion connecting the top side to the bottom side and the large diameter top opening to the small diameter bottom opening so that the sight glass has a hollow, substantially frustoconically shaped interior when fluid is not in the drainable sight glass assembly, and a substantially cylindrical exterior, e.g., as shown in FIGS. 11 and 12.

In some embodiments of the invention, a sight glass housing 1102 can be a portion of the drainable sight glass assembly 1100 comprising a vessel that is capable of holding a fluid drained from the housing. As such, the sight glass housing 1102 can include an upper disk layer 1108, a lower disk portion 1110, and a sight glass body 1112. The upper disk layer 1108 can be a substantially cylindrically shaped body, having a diameter greater than its length, and adapted to receive an upper valve (discussed below) to attach the sight glass to the pump housing. Accordingly, the upper disk layer 1108 can be disposed on a top side 1114 of the sight glass housing 1102 in abutting contact with the sight glass body 1112, and can have a threaded receptacle 1123 formed substantially in the center thereof for receiving the upper valve. The upper disk layer 1108 substantially can cover and seal a large diameter opening 1116 in the sight glass body 1112 when the drainable sight glass assembly 1100 is disposed in communication with the housing drain port and the upper valve 1104 is not open to the sight glass housing 1102.

In some embodiments, the large diameter opening 1116 can be sized to have a diameter between 1.0 inches to 2.5 inches, and the upper disk layer 1108 can be sized to have a diameter between 1.4 inches to 3.0 inches if, for example, the sight glass body 1112 is designed to have an overall height between 3 to 4 inches and a an interior height of 2.5 inches, to hold a one to three ounce testing volume. As one skilled in the art will recognize, the upper disk layer 1108 used in such a drainable sight glass assembly 1100 can have a thickness or length between 0.25 to 0.7 inches. In some embodiments, the upper disk layer 1108 has a threaded receptacle 1123 formed therein for receiving either the complementary threads of the housing drain port or the upper valve 1104. The upper disk layer 1108 can be manufactured from acrylic, polytetrafluoroethylene (e.g., Teflon®), steel, aluminum, brass, copper, and other similar materials using, e.g., extrusion techniques, welding, molding, die casting and other known manufacturing techniques as appropriate for the material and application of use for the drainable sight glass assembly 1100.

As further shown, in some embodiments, the sight glass housing 1102 includes a lower disk portion 1110. The lower disk portion 1110 can be a substantially cylindrically shaped body, having a diameter greater than its length, and adapted to receive a lower valve (discussed below) to drain water from the pump housing. The lower disk portion 1110 can have disposed substantially in the center thereof a threaded receptacle 1121, which can be designed to receive the lower valve 1106, and accordingly, the lower disk portion 1110 is disposed on a bottom side 1117 of and in abutting contact with the sight glass body 1112. The lower disk portion 1110 formed to, e.g., substantially cover, and seal a small diameter opening 1119 in the sight glass housing when the sight glass housing 1102 is disposed in communication with the lower valve 1106, and the lower valve 1106 is not open to the sight glass housing 1102, e.g., is not in a position to drain the sight glass housing 1102.

In some embodiments, the small diameter opening 1119 of the sight glass body 1110 can be sized to have a diameter between 0.4 inches to 0.75 inches, and the lower disk portion can be sized to have a diameter substantially similar to the upper disk layer 1108, if, e.g., the sight glass body 1112 is designed to have an overall height between 3 to 4 inches and an interior height of 2.5 inches, to, for example, hold a one to three ounce testing volume. As one skilled in the art will recognize, a lower disk portion used in such an exemplary sight glass can have a thickness or length between 0.25 to 0.7 inches. In some embodiments, the lower disk portion 1110 can also have the threaded receptacle 1121 formed therein for receiving the complementary threads of the lower valve 1106. The lower disk portion 1110 can be manufactured from acrylic, polytetrafluoroethylene (e.g., Teflon®), steel, aluminum, brass, copper, and other similar materials using, e.g., extrusion techniques, welding, molding, die casting and other known manufacturing techniques as appropriate for the material and application of use for the drainable sight glass assembly 1100.

Returning to the Figures, the sight glass body 1112 is connected to the upper disk layer 1108 and lower disk portion 1110 and comprises an upper side 1130 that has the large diameter opening formed therein and a lower side 1132 that has the small diameter opening formed therein, and a wall portion 1134. As previously mentioned, the upper diameter opening can be sized between the small diameter opening 1117 can be sized to be between 0.4 inches to 0.75 inches, and the large diameter opening can be sized to be between 1.0 inches to 2.5 inches, if, e.g., the sight glass body 1112 is designed to have an overall height between 3 to 4 inches and a an interior height of 2.5 inches, to, e.g., hold a one to three ounce testing volume. The exterior of the upper side and lower side of the sight glass body 1112 can have measurements to match the upper disk layer 1108 and lower disk portion 1110, e.g., a similar top and bottom diameter, giving the sight glass body wall a thickness of no less then, e.g., 0.2 inches. In some embodiments, the exterior of the upper side and lower side can be smaller than the corresponding upper disk layer 1108 and lower disk portion 1110, e.g., when the upper disk layer 1108 and lower disk portion 1110 include flanges that circumscribe and extend over a portion of the sight glass body 1112 to allow the upper disk layer 1108 and lower disk portion 1110 to connect to the sight glass body 1112 using, e.g., adhesive. As one skilled in the art will appreciate, the sight glass body 1112 is preferably manufactured from a transparent material that is in each case suited for the application in which the sight glass body 1112 is installed. For example, in high temperature applications, e.g., for temperatures exceeding 150 degrees Fahrenheit, the sight glass body 1112 can be manufactured from, e.g., pyrex, while in other applications, the sight glass body 1112 can be manufactured from, for example, acrylic, glass, or the like. Depending upon the material used, the sight glass body 1112 can be manufactured using known extrusion, injection molding, compression molding and pressing and blowing techniques.

As one skilled in the art will recognize, the upper disk layer 1108 and lower disk portion 1110 can be adhered to the sight glass body 1112 using, for example, adhesive such as, for example, cyanoacrylate cement, more commonly known as superglue, or epoxy resin; with heat (welding or annealing); or by using solvents such as dichloromethane or trichloromethane, depending upon the material used for the upper disk layer 1108, lower disk portion 1110, and sight glass body 1112. As one skilled in the art will also appreciate, some of the above embodiments of the upper disk layer 1108 and lower disk portion 1110 are for applications where the fluid tested is not at an extreme temperature, or the type of fluid is not volatile. As such, embodiments of the invention can include sight glasses acceptable for extreme temperature or volatile fluid applications, and as such, the upper disk layer 1108 and lower disk portion 1110 can be machined and connected to the sight glass body 1112 in such a manner to protect the sight glass body 1112.

For example, the upper disk layer 1108 and lower disk portion 1110 can be fabricated from, e.g., steel or polytetrafluoroethylene (e.g., Teflon®), and connected to the sight glass body 1112 using an industrial type of adhesive capable of withstanding high temperature. In other embodiments, the upper disk layer 1108 and lower disk portion 1110 may be machined with a larger diameter than the sight glass body 1112 so that a portion of the upper disk layer 1108 and lower disk portion 1110 extends past an exterior edge of the sight glass body 1112. In such an embodiment, the upper disk layer 1108 and lower disk portion 1110 may have a plurality of holes formed in the portion of the upper disk layer 1108 and lower disk portion 1110 extending past the sight glass body 1112 to accommodate a plurality of screws that may connect the upper disk layer 1108 and lower disk portion 1110 around the periphery of the sight glass body 1112, and secure same using, e.g., bolts, as is known in the art.

In other embodiments, the upper disk layer 1108 and lower disk portion 1110 can be formed from the same material as the wall portion 1134 using, e.g., an extrusion technique, so that the upper disk layer 1108, lower disk portion 1110 and wall portion 1134 are formed as an integral unit and, when connected to the upper valve 1104 and lower valve 1106, form a vessel capable of being sealed. In other embodiments, the upper disk layer 1108 and lower disk portion 1110 may have a colored coating disposed thereon so that water in the sight glass may be easily viewed. In any case, when the upper disk layer 1108 and bottom disk layer are joined to the sight glass body 1112 using, for example, the methods described above, the drainable sight glass assembly 1102 has a hollow, substantially frustoconically shaped interior 90 when fluid is not in the drainable sight glass assembly 1102.

The use of the sight glass 100 will now be described with reference to the Figures. A method for using a sight glass with, for example, an oil sump pump, oil reservoir or diesel reservoir, to monitor the condition of oil in a housing and to drain water from such a housing, the sight glass being connected to a drain port located on a housing body that is in communication with an oil reservoir in the housing, may comprise the steps of: connecting an upper valve 104 positioned in a sight glass housing to the drain port of the housing, positioning on a bottom side with a small diameter bottom opening sealed with a lower disk portion 110 in a second threaded receptacle formed therein, a lower valve 106; draining oil into the sight glass using the upper valve 104 in conjunction with the housing drain port; viewing the contents of the sight glass to determine the condition of the oil in the sight glass and whether or not water is present; turning the lower portion of the stem handle of the lower valve 106 when it is determined that water is in the sight glass to dispose the top portion of the stem substantially inside the valve housing to drain water from the sight glass; removing the sight glass from the housing drain plug, responsive to the water being drained; testing the oil in the sight glass to determine a mechanical cause for any contaminants being present in the oil; removing the sight glass from the housing drain plug; reintroducing the oil in the sight glass to the housing when the water is drained from the sight glass and when it is determined that the condition of the oil in the sight glass is acceptable for continued use; and cleaning the sight glass so that any residue formed thereon by the oil and any contaminants is removed; and reattaching the sight glass to the housing drain plug.

Figure 13:
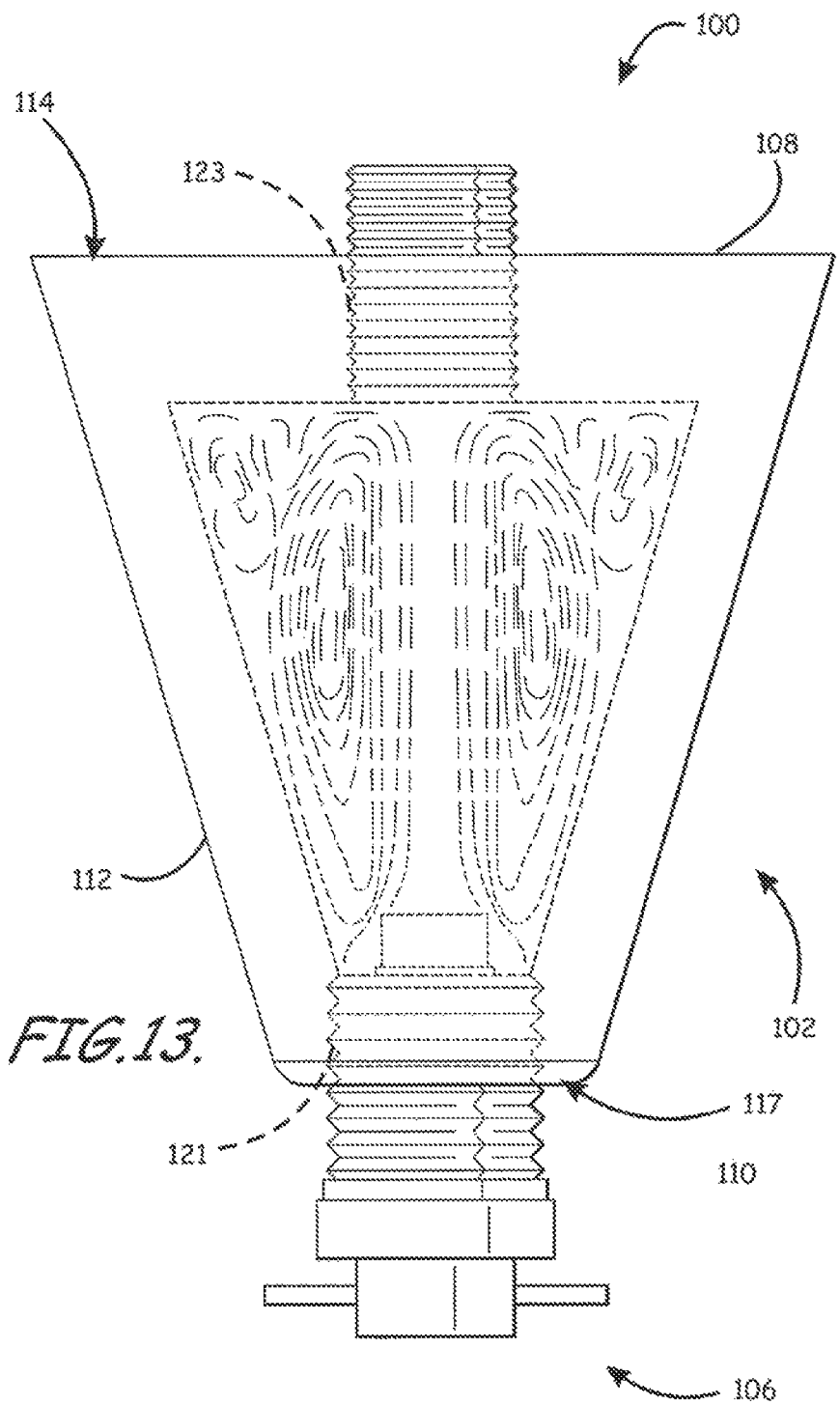
FIG. 13 is a side view of a sight glass having a frustoconically shaped interior showing a turbulent flow of a fluid being drained into the sight glass body according to an embodiment of the invention.

As shown in FIG. 13, the frustoconically shaped interior of the sight glass has an improved turbulent flow pattern for liquid disposed therein, and aids with sediment settling toward a bottom of the sight glass. As can be seen, the shape of the sight glass interior according to embodiments described herein allows the sediment to settle, water and, e.g., fluid, to separate, and an operator to more quickly access the condition of the fluid and any remedies thereto, e.g., draining water, testing additional equipment, etc.

Figure 20:
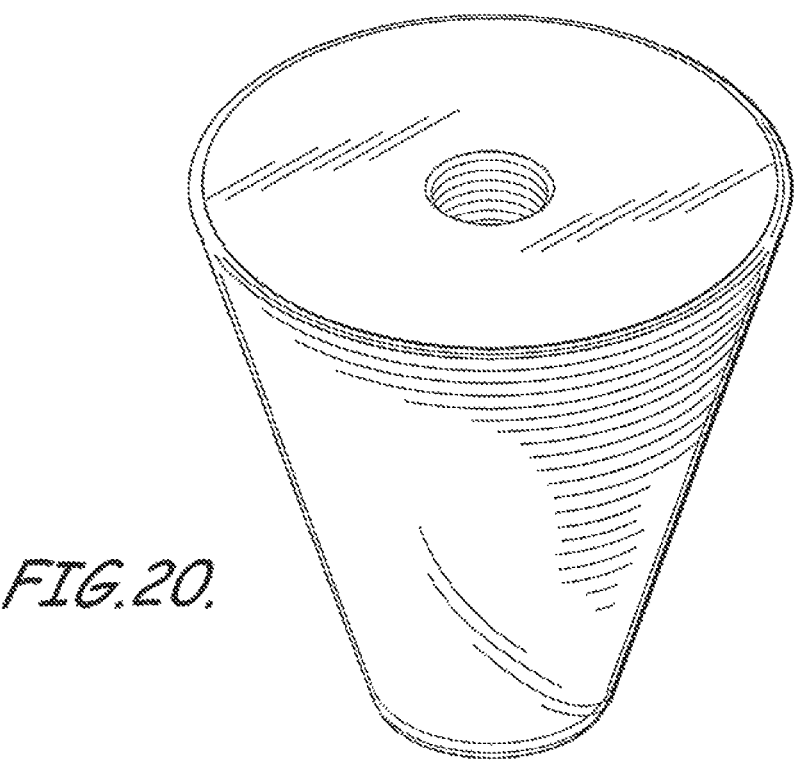
FIG. 20 is a top perspective view of a sight glass body having a frustoconically shaped interior according to an embodiment of the invention.
Figure 21:
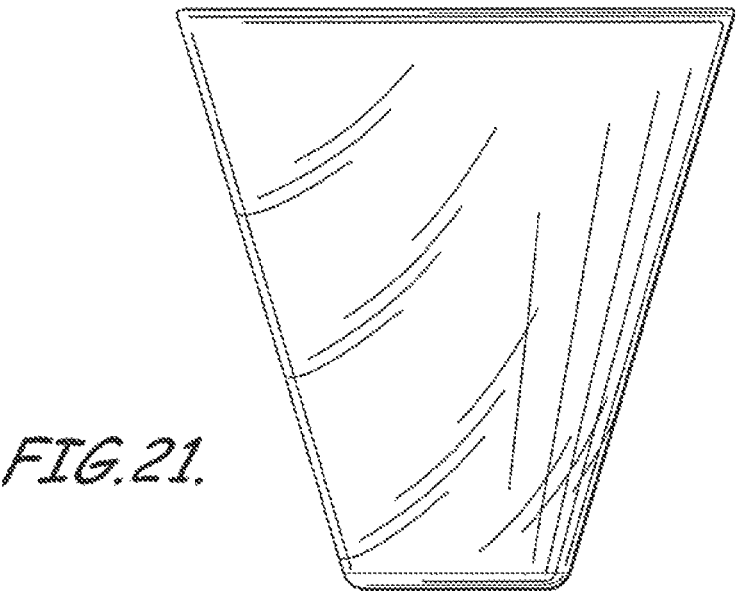
FIG. 21 is a side view of a sight glass body having a frustoconically shaped interior according to an embodiment of the invention.
Figure 22:
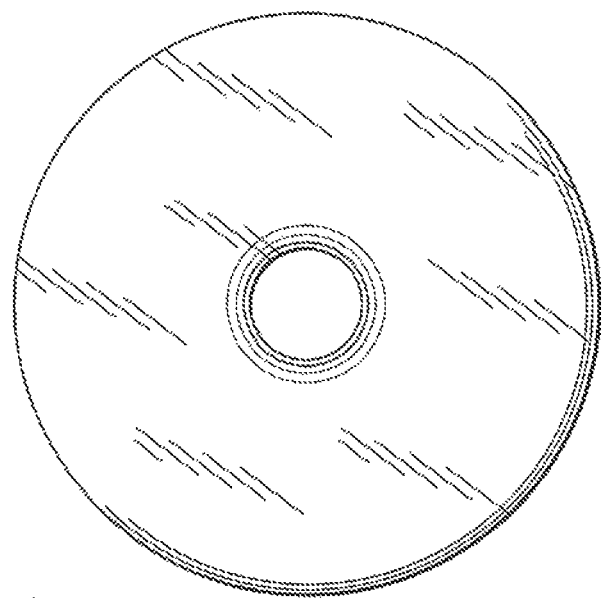
FIG. 22 is a top view of a sight glass body having a frustoconically shaped interior according to an embodiment of the invention.
Figure 23:
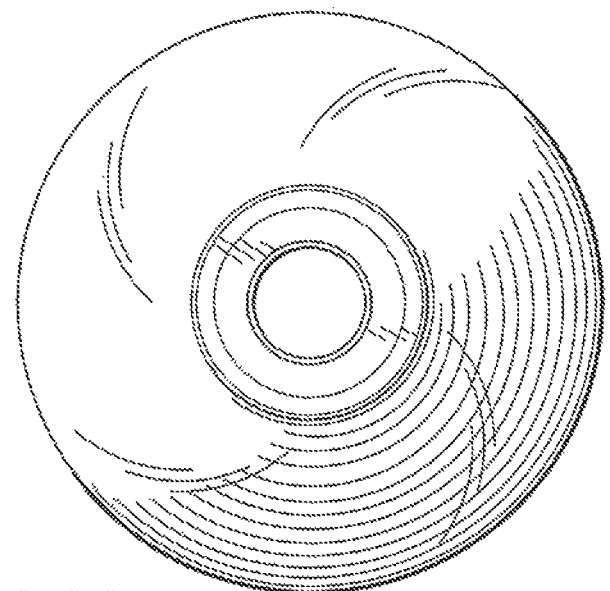
FIG. 23 is a bottom view of a sight glass body having a frustoconically shaped interior according to an embodiment of the invention.

FIG. 14 is a side view of a sight glass having a frustoconically shaped interior showing a fluid being drained from the sight glass body according to an embodiment of the invention. FIG. 15 is a side view of a sight glass body having a frustoconically shaped interior showing threads in the sight glass body for receiving a lower valve according to an embodiment of the invention. FIG. 16 is a side view of a sight glass having a frustoconically shaped interior showing a fluid being drained from the sight glass body according to an embodiment of the invention. FIG. 17 is a side view of a sight glass body having a frustoconically shaped interior showing threads in the sight glass body for receiving a lower valve according to an embodiment of the invention. FIG. 18 is a top perspective view of a sight glass body having a frustoconically shaped interior according to an embodiment of the invention. FIG. 19 is a side view of a sight glass body having a frustoconically shaped interior according to an embodiment of the invention. FIG. 20 is a top view of a sight glass body having a frustoconically shaped interior according to an embodiment of the invention. And, FIG. 21 is a bottom view of a sight glass body having a frustoconically shaped interior according to an embodiment of the invention.

In the drawings and specification, there have been disclosed some typical preferred embodiments of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification.

That claimed is:

1. A drainable sight glass assembly to view the condition of fluid when disposed within a vessel, the drainable sight glass assembly comprising:
   a sight glass housing including an upper disk layer having a first diameter and a first receptacle, a lower disk portion having a second diameter and a second receptacle, and a substantially transparent wall portion connecting the upper disk layer to the lower disk portion;
   an upper valve connected to the first receptacle, the upper valve for controlling fluid into the sight glass housing;
   a lower valve connected to the second receptacle for controlling fluid flow out of the sight glass housing; and a measurement assembly adapted to determine the level of fluid in the sight glass housing;

the sight glass housing having a frustoconically shaped interior that tapers to a minimum diameter at a lower end substantially equal to the diameter of the lower valve; and the upper valve having one port connected to the sight glass housing, and one port connected to the measurement assembly.

2. The drainable sight glass assembly of claim 1, wherein the upper disk layer, wall portion, and lower disk portion are integrally formed.

3. The drainable sight glass assembly of claim 1, wherein the upper disk layer is connected to the wall portion using adhesive, heat treatment, or solvents, the adhesive selected from the group consisting of cyanoacrylate cement and epoxy resin, the heat treatment selected from the group consisting of welding and annealing, and the solvent selected from the group consisting of dichloromethane and trichloromethane.

4. The drainable sight glass assembly of claim 1, wherein the lower valve is a three-way valve, having one port connected to the sight glass housing, one port connected to a sample vessel, and one port open to act as a drain.

5. The drainable sight glass assembly of claim 1, wherein the upper valve has an upper valve stem connected to an upper valve housing, the upper valve housing having three ports, including a first port connected to the first receptacle, a second port connected to the measurement assembly for measuring the volume of oil in the sight glass housing, and a third port connected to the upper valve stem, the upper valve housing operable to selectively direct a flow of fluid to the drainable sight glass assembly or to the measurement assembly.

6. The drainable sight glass assembly of claim 5, wherein the drainable sight glass assembly is vented to relieve pressure from the drainable sight glass assembly and allow the upper valve housing to switch the flow of fluid from the drainable sight glass assembly to the measurement assembly.

7. A drainable sight glass housing for viewing fluid in a vessel, the drainable sight glass housing comprising:

an upper disk layer having a first outer diameter and a first receptacle; a lower disk portion having a second outer diameter and a second receptacle;

a substantially transparent wall portion connecting the upper disk layer to the lower disk portion and having a substantially frustoconically shaped interior profile;

a lower valve connected to the second receptacle, the lower valve operable to control fluid flow out of the sight glass housing; and a measurement assembly adapted to determine the level of fluid in the housing:

the upper valve having one port connected to the sight glass housing, and one port connected to the measurement assembly.

8. The drainable sight glass housing of claim 7, further comprising:

an upper valve connected to the first receptacle, the upper valve having an upper stem connected to the vessel and operable to control fluid flow into the sight glass housing.

9. The drainable sight glass housing of claim 8, wherein the lower valve portion is a three-way valve, having one port connected to the sight glass housing, one port connected to a sample vessel, and one port open to act as a drain.

10. The drainable sight glass housing of claim 8, wherein the upper valve has an upper valve stem connected to an upper valve housing, the upper valve housing having three ports, including a first port connected to the first receptacle, a second port connected to the measurement assembly for measuring the volume of oil in the sight glass housing, and a third port connected to the upper valve stem, the upper valve housing operable to selectively direct a flow of fluid to the drainable sight glass assembly or to the measurement assembly.

11. The drainable sight glass housing of claim 10, wherein the drainable sight glass assembly is vented to relieve pressure from the drainable sight glass assembly and allow the upper valve housing to switch the flow of fluid from the drainable sight glass assembly to the measurement assembly.

12. The drainable sight glass housing of claim 7, wherein the first and second outer diameters are substantially the same; and wherein the upper disk layer, wall portion, and lower disk portion are integrally formed.

13. The drainable sight glass housing of claim 7, wherein the upper disk layer is connected to the wall portion using adhesive, heat treatment, or solvents, the adhesive selected from the group consisting of cyanoacrylate cement and epoxy resin, the heat treatment selected from the group consisting of welding and annealing, and the solvent selected from the group consisting of dichloromethane and trichloromethane.

14. A method for using a drainable sight glass assembly with a vessel to monitor the condition of a fluid in the vessel, the method comprising the steps of:

connecting a drainable sight glass assembly including a sight glass housing to the drain port of the vessel, the sight glass housing having a substantially frustoconically-shaped interior that tapers to a minimum diameter at a lower end, and that does not have interior shoulders capable of trapping debris in the sight glass;

draining fluid from the vessel into the drainable sight glass assembly so that the fluid enters the frustoconically-shaped interior of the sight glass housing;

waiting for particulate in the fluid to settle at a bottom of the frustoconically-shaped interior portion;

viewing the fluid in the sight glass housing to determine a condition of the fluid in the sight glass housing;

removing the drainable sight glass assembly from the vessel:

separating the water and oil from the sight glass housing, so that the oil can be tested:

cleaning the sight glass assembly so that any residue and particulate is removed; and reattaching the drainable sight glass assembly to the vessel.

15. The method of claim 14, further comprising:

determining whether or not water is present in the sight glass housing; and draining the sight glass assembly using a valve positioned at the bottom thereof.

16. The method of claim 14, further comprising:

removing the sight glass assembly from the vessel; and testing the fluid and particulates in the sight glass housing to determine the composition of the fluid and particulates.

* * * * *